(12) United States Patent
Vollmer

(10) Patent No.: US 12,161,485 B2
(45) Date of Patent: Dec. 10, 2024

(54) PATIENT MONITORING APPARATUS

(71) Applicant: KONINKLIJKE PHILIPS N.V., Eindhoven (NL)

(72) Inventor: Thomas Vollmer, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 891 days.

(21) Appl. No.: 16/333,266

(22) PCT Filed: Sep. 28, 2017

(86) PCT No.: PCT/EP2017/074728
§ 371 (c)(1),
(2) Date: Mar. 14, 2019

(87) PCT Pub. No.: WO2018/060394
PCT Pub. Date: Apr. 5, 2018

(65) Prior Publication Data
US 2019/0246924 A1    Aug. 15, 2019

(30) Foreign Application Priority Data
Sep. 28, 2016   (EP) ..................... 16191086

(51) Int. Cl.
*A61B 18/12*   (2006.01)
*A61B 5/00*    (2006.01)
(Continued)

(52) U.S. Cl.
CPC ............ *A61B 5/7203* (2013.01); *A61B 5/318* (2021.01); *A61B 18/1206* (2013.01);
(Continued)

(58) Field of Classification Search
CPC ... A61B 5/318; A61B 5/7203; A61B 5/02416; A61B 18/1206; A61B 2018/00839; A61B 2018/1293
See application file for complete search history.

(56) References Cited

U.S. PATENT DOCUMENTS 4,304,073 A    12/1981   Archibald
4,800,894 A     1/1989   Milani
(Continued)

FOREIGN PATENT DOCUMENTS

EP        0707825          4/1996
JP     2009061179 A    *   3/2009
(Continued)

OTHER PUBLICATIONS

Yang et al: "Sensor Fusion Using a Hybrid Median Filter for Artifact Removal in Intraoperative Heart Rate Monitoring", Journal of Clinical Monitoring and Computing, Kluwer Academic Publishers, DO, vol. 23, No. 2, Feb. 7, 2009.
(Continued)

*Primary Examiner* — Thomas A Giuliani
*Assistant Examiner* — Christine A Dedoulis

(57) ABSTRACT

The invention relates to a patient monitoring apparatus (6) comprising a first measuring unit (7) for performing an electrical measurement of a physiological property like an electrocardiogram measurement providing a heart rate, while an electrical treatment procedure is not performed, and a second measuring unit (8) for performing a non-electrical measurement of the physiological property like an optical photoplethysmogram measurement providing the heartrate. A data communication unit (10) is adapted to receive a treatment indication, which indicates that the electrical treatment procedure will be performed, from an electrical treatment apparatus (12), and a controller (9) is adapted to control the patient monitoring apparatus such that the mea-
(Continued)

surement of the physiological property is switched from the electrical measurement to the non-electrical measurement, after the treatment indication has been received. This allows for an improved patient monitoring, because the likelihood of disturbance by, for instance, electrical noise can be significantly reduced.

11 Claims, 2 Drawing Sheets

(51) Int. Cl.
*A61B 5/024* (2006.01)
*A61B 5/318* (2021.01)
*A61B 5/1455* (2006.01)
*A61B 18/00* (2006.01)

(52) U.S. Cl.
CPC ....... *A61B 5/02416* (2013.01); *A61B 5/14551* (2013.01); *A61B 2018/00351* (2013.01); *A61B 2018/00595* (2013.01); *A61B 2018/00839* (2013.01); *A61B 2018/1293* (2013.01)

(56) References Cited

U.S. PATENT DOCUMENTS

| | | | | |
|---|---|---|---|---|
| 5,357,956 | A | * | 10/1994 | Nardella ................ A61B 18/12 607/9 |
| 6,052,614 | A | | 4/2000 | Morris |
| 6,383,183 | B1 | * | 5/2002 | Sekino ............... A61B 18/1206 606/34 |
| 2003/0135087 | A1 | | 7/2003 | Hickle |
| 2007/0197878 | A1 | | 8/2007 | Shklarski |
| 2009/0069642 | A1 | | 3/2009 | Gao |
| 2010/0179541 | A1 | * | 7/2010 | Joseph .................. G09B 23/28 606/42 |
| 2014/0128757 | A1 | * | 5/2014 | Banet .................. A61B 5/0006 600/513 |
| 2016/0011244 | A1 | * | 1/2016 | Buck ................. A61B 18/1206 324/76.11 |

FOREIGN PATENT DOCUMENTS

| | | |
|---|---|---|
| JP | 2013017752 A | 1/2013 |
| WO | 94/09698 | 5/1994 |
| WO | 2015/150199 | 10/2015 |

OTHER PUBLICATIONS

Dumont: "Signal Processing and Automation in Anesthesia [Life Sciences]", IEEE Signal Processing Magazine, IEEE Service Center, Piscataway, NJ, US, vol. 32, No. 4, Jul. 1, 2015.

Petersen et al: "Reducing Risk During Endoscopy in Patients with Implanted Electronic Devices", Techniques in Gastrointestinal Endoscopy, vol. 9, No. 4, Nov. 1, 2007.

Buschke et al: "An Innovative Web Services-Based Architecture for Distributed Systems of Medical Devices" White Paper HIMSS 2015.

Medtronic Electrosurgical Hardware, http://www.medtronic.com/covidien/products/electrosurgical-hardware.

Medtronic Electrosurgical Instruments, http://www.medtronic.com/covidien/products/electrosurgical-instruments.

* cited by examiner

PATIENT MONITORING APPARATUS

CROSS REFERENCE TO RELATED APPLICATIONS

This application is the U.S. National Phase application under 35 U.S.C. § 371 of International Application No. PCT/EP2017/074728 filed Sep. 28, 2017, published as WO 2018/060394 on Apr. 5, 2018, which claims the benefit of European Patent Application Number 16191086.4 filed Sep. 28, 2016. These applications are hereby incorporated by reference herein.

FIELD OF THE INVENTION

The invention relates to a patient monitoring apparatus, method and computer program for monitoring a patient. The invention relates further to an electrical treatment apparatus for performing an electrical treatment procedure and a system comprising the patient monitoring apparatus and the electrical treatment apparatus.

BACKGROUND OF THE INVENTION

A patient monitoring apparatus is, for instance, an apparatus for monitoring a heart rate of a patient based on an electrocardiogram (ECG). If the heart rate is monitored by using the electrocardiogram during an electrosurgical procedure, the heart rate monitoring can be frequently disturbed by radiofrequency noise produced by electrosurgical equipment. This is critical for patient safety as heart rate information is missing during the invasive electrosurgical procedure.

WO 94/09698 A1 discloses a method for adapting to noise in a signal obtained with an active signal sensing monitor having a demultiplexer. The demultiplexer selects between two signals at a demultiplexer frequency. The method comprises determining a noise level at a first selected demultiplexer frequency, determining noise levels at one or more other selected demultiplexer frequencies and comparing the noise levels of the first and other demultiplexer frequencies. An optimum demultiplexer frequency having a comparatively low noise level is selected from among the first and one or more other demultiplexer frequencies, wherein the active signal sensing monitor is operated at the selected optimum demultiplexer frequency.

SUMMARY OF THE INVENTION

It is an object of the present invention to provide a patient monitoring apparatus, method and computer program which allow for an improved patient monitoring during an electrical treatment procedure. It is a further object of the present invention to provide an electrical treatment apparatus for performing an electrical treatment procedure and a system comprising the patient monitoring apparatus and the electrical treatment apparatus.

In a first aspect of the present invention a patient monitoring apparatus for monitoring a patient is presented, wherein the patient monitoring apparatus comprises:
- a first measuring unit for performing an electrical measurement of a physiological property of a patient, while an electrical treatment procedure is not performed,
- a second measuring unit for performing a non-electrical measurement of the physiological property of the patient, while the electrical treatment procedure is performed,
- a data communication unit for receiving a treatment indication, which indicates that the electrical treatment procedure will be performed, from an electrical treatment apparatus,
- a controller for controlling the patient monitoring apparatus such that the measurement of the physiological property is switched from the electrical measurement to the non-electrical measurement, after the treatment indication has been received.

Since the data communication unit is adapted to receive a treatment indication, which indicates that the electrical treatment procedure will be performed, from the electrical treatment apparatus and since the controller is adapted to control the patient monitoring apparatus such that the measurement of the physiological property is switched from the electrical measurement to the non-electrical measurement, after the treatment indication has been received, during the electrical treatment procedure the physiological property will be measured by a non-electrical measurement. Thus, while performing the electrical treatment procedure, the measurement of the physiological property cannot be disturbed anymore by, for instance, electrical noise, thereby improving the patient monitoring.

Preferentially, the data communication unit is adapted to receive the treatment indication, which indicates that the electrical treatment procedure will be performed, from an electrical treatment apparatus as defined in claim 7.

The electrical measurement of the physiological property of the patient is carried out by measuring an electrical physiological activity of the patient, from which the physiological property is derived. The non-electrical measurement of the physiological property of the patient is carried out by measuring a non-electrical physiological activity of the patient, from which the physiological property is derived. The term "electrical" in the expression "electrical measurement" and the term "non-electrical" in the expression "non-electrical measurement" therefore refer to the kind of physiological activity which is measured for measuring the physiological property. For instance, the physiological property can be the heart rate of the patient, which can be measured by measuring an electrocardiogram, i.e. by measuring an electrical physiological activity, or which can be measured by optically measuring a photoplethysmogram, i.e. by measuring a non-electrical physiological activity. The electrical treatment procedure is preferentially an electrosurgical procedure, an electrocautery procedure or another electrical treatment procedure which generates a disturbance of the electrical measurement of the physiological property.

Preferentially, the controller is adapted to control the patient monitoring apparatus such that the data communication unit sends a non-electrical measurement indication, which indicates that the second measuring unit measures the physiological property, to the electrical treatment apparatus, after the measurement of the physiological property has been switched from the electrical measurement to the non-electrical measurement. Thus, the patient monitoring apparatus can inform the electrical treatment apparatus that the measurement mode has been switched from the electrical measurement to the non-electrical measurement. This information can be used by the electrical treatment apparatus to start the electrical treatment procedure only, if it has received this information indicating that the non-electrical measurement is really active. This further ensures that during performing the electrical treatment procedure the non-electrical measurement is carried out and not the electrical measurement.

Moreover, the controller is preferentially adapted to control the patient monitoring apparatus such that the data communication unit receives a completion indication, which indicates that the electrical treatment procedure has been completed, from the electrical treatment apparatus and the measurement of the physiological property is switched from the non-electrical measurement to the electrical measurement, after the completion indication has been received. Thus, the electrical treatment apparatus can inform the patient monitoring apparatus that the electrical treatment procedure has been completed such that the patient monitoring apparatus can switch back from the non-electrical measurement to the electrical measurement. This can further ensure that the non-electrical measurement is performed, only if the electrical treatment procedure is carried out. In particular, if the electrical treatment procedure is repeatedly carried out, the patient monitoring apparatus may repeatedly switch between the electrical measurement and the non-electrical measurement such that each time the electrical treatment procedure is carried out the physiological property is non-electrically measured and at other times the physiological property is electrically measured.

In another aspect of the present invention an electrical treatment apparatus for performing an electrical treatment procedure is presented, wherein the electrical treatment apparatus comprises:
- an electrical energy source for providing electrical energy to a treatment device for performing the electrical treatment procedure,
- a data communication unit for sending a treatment indication, which indicates that the electrical treatment procedure will be performed, to a patient monitoring apparatus,
- a controller for controlling the electrical treatment apparatus such that the data communication unit sends the treatment indication to the patient monitoring apparatus, before the electrical treatment procedure is performed.

Since the data communication unit is adapted to send a treatment indication, which indicates that the electrical treatment procedure will be performed, to the patient monitoring apparatus and since the controller is adapted to control the electrical treatment apparatus such that the data communication unit sends the treatment indication to the patient monitoring apparatus, before the electrical treatment procedure is performed, the patient monitoring apparatus can itself switch from the electrical measurement to the non-electrical measurement, before the electrical treatment procedure is performed, thereby allowing for a prevention of a disturbance of the monitoring of the physiological property by, for instance, electrical noise during performing the electrical treatment procedure. This allows for an improved patient monitoring, while the electrical treatment procedure is carried out.

The electrical energy source is preferably a radiofrequency energy source proving radiofrequency energy for carrying out an electrosurgical procedure. The electrical energy source is preferably adapted to be connected to an electrosurgical instrument which actually carries out the electrosurgical procedure. However, the electrical energy source can also be adapted to provide electrical energy for carrying out another kind of electrical treatment procedure like an electrocautery procedure. For instance, the electrical energy source can be adapted to provide a direct or alternating electrical current to an electrocautery instrument like a metal probe in order to heat the electrocautery instrument, wherein the heat is used for the cauterization. In this case the electrical energy source might be, for instance, a high frequency energy source.

Preferentially, the data communication unit is adapted to send the treatment indication, which indicates that the electrical treatment procedure will be performed, to a patient monitoring apparatus as defined in claim 1.

Preferentially, the controller of the electrical treatment apparatus is adapted to control the electrical treatment apparatus such that the data communication unit receives a non-electrical measurement indication, which indicates that the second measuring unit of the patient monitoring apparatus measures the physiological property, from the patient monitoring apparatus and the electrical energy source provides the electrical energy, after the non-electrical measurement indication has been received. Thus, it can be further ensured that the electrical treatment procedure is performed, only if the non-electrical measurement of the physiological property is carried out, thereby further improving the patient monitoring process.

It is preferred that the controller is adapted to control the electrical treatment apparatus such that the data communication unit sends a completion indication, which indicates that the electrical treatment procedure has been completed, to the patient monitoring apparatus, after the electrical treatment procedure has been completed. This gives the patient monitoring apparatus a clear indication, when it can switch back to the electrical measurement of the physiological property, thereby allowing for a further improved patient monitoring process.

It is further preferred that the electrical treatment apparatus comprises a user interface for allowing a user to indicate that the electrical treatment procedure will be started, wherein the controller is adapted to control the electrical treatment apparatus such that the data communication unit sends the treatment indication, after the user has indicated that the electrical procedure will be started. For instance, the electrical treatment apparatus can comprise a foot switch or another input device as a user interface which allows the user to indicate that the electrical treatment procedure will be started. Thus, for example, each time the user actuates a foot switch, firstly a treatment indication, which indicates that the electrical treatment procedure will be performed, is sent to the patient monitoring apparatus, secondly the electrical treatment apparatus receives a non-electrical measurement indication, which indicates that the second measuring unit of the patient monitoring apparatus measures non-electrically the physiological property, i.e. by measuring a non-electrical physiological activity, and thirdly, only if this non-electrical measurement indication has been received by the electrical treatment apparatus, the electrical treatment procedure is started. Thus, by using the foot switch or another user interface this data communication, i.e. this exchange of the indications, might be started, and only if the electrical treatment apparatus has received the non-electrical measurement indication, the electrical treatment procedure begins.

In a further aspect of the present invention a system for monitoring a patient and for performing an electrical treatment procedure is presented, wherein the system comprises:
- an electrical treatment apparatus for performing the electrical treatment procedure as defined in claim 7,
- a patient monitoring apparatus for monitoring a patient as defined by claim 1.

In a further aspect of the present invention a patient monitoring method for monitoring a patient by using the patient monitoring apparatus as defined in claim 1 is presented, wherein the patient monitoring method comprises:
- performing an electrical measurement of a physiological property of a patient, while an electrical treatment procedure is not performed, by the first measuring unit of the patient monitoring apparatus,
- performing a non-electrical measurement of the physiological property of the patient, while the electrical treatment procedure is performed, by the second measuring unit of the patient monitoring apparatus,
- receiving a treatment indication, which indicates that an electrical treatment procedure will be performed, from an electrical treatment apparatus as defined in claim 7 by the data communication unit of the patient monitoring apparatus,
- controlling the patient monitoring apparatus such that the measurement of the physiological property is switched from the electrical measurement to the non-electrical measurement, after the treatment indication has been received, by the controller of the patient monitoring apparatus.

The invention relates also to a communication method for communicating between a patient monitoring apparatus as defined in claim 1 and an electrical treatment apparatus as defined in claim 7, wherein the communication method comprises:
- sending a treatment indication, which indicates that an electrical treatment procedure will be performed, to the patient monitoring apparatus by the data communication unit of the electrical treatment apparatus,
- controlling the electrical treatment apparatus such that the data communication unit sends the treatment indication to the patient monitoring apparatus, before an electrical treatment procedure is performed, by the controller of the electrical treatment apparatus.

This method might also be regarded as being a method for operating the electrical treatment apparatus as defined in claim 7, wherein the method comprises a) sending a treatment indication, which indicates that an electrical treatment procedure will be performed, to the patient monitoring apparatus by the data communication unit of the electrical treatment apparatus, and b) controlling the electrical treatment apparatus such that the data communication unit sends the treatment indication to the patient monitoring apparatus, before an electrical treatment procedure is performed, by the controller of the electrical treatment apparatus.

In a further aspect of the present invention a computer program for monitoring a patient by using the patient monitoring apparatus as defined in claim 1 is presented, wherein the computer program comprises program code means for causing the patient monitoring apparatus to carry out patient monitoring methods described herein, when the computer program is run on the patient monitoring apparatus.

The invention also relates to a computer program for communicating between a patient monitoring apparatus as defined in claim 1 and an electrical treatment apparatus as defined in claim 7, wherein the computer program comprises program code means for causing the electrical treatment apparatus to carry out the communication methods described herein, when the computer program is run on the electrical treatment apparatus.

It shall be understood that the patient monitoring apparatus of claim 1, the electrical treatment apparatus of claim 7, the system for monitoring a patient and for performing an electrical treatment procedure of claim 11, the patient monitoring methods described herein, the communication methods described herein, the computer programs for monitoring a patient described herein and the computer programs for communicating between a patient monitoring apparatus and an electrical treatment apparatus described herein have similar and/or identical preferred embodiments, in particular, as described herein and in some of the dependent claims.

These and other aspects of the invention will be apparent from and elucidated with reference to the embodiments described hereinafter.

DETAILED DESCRIPTION OF EMBODIMENTS

Figure 1:
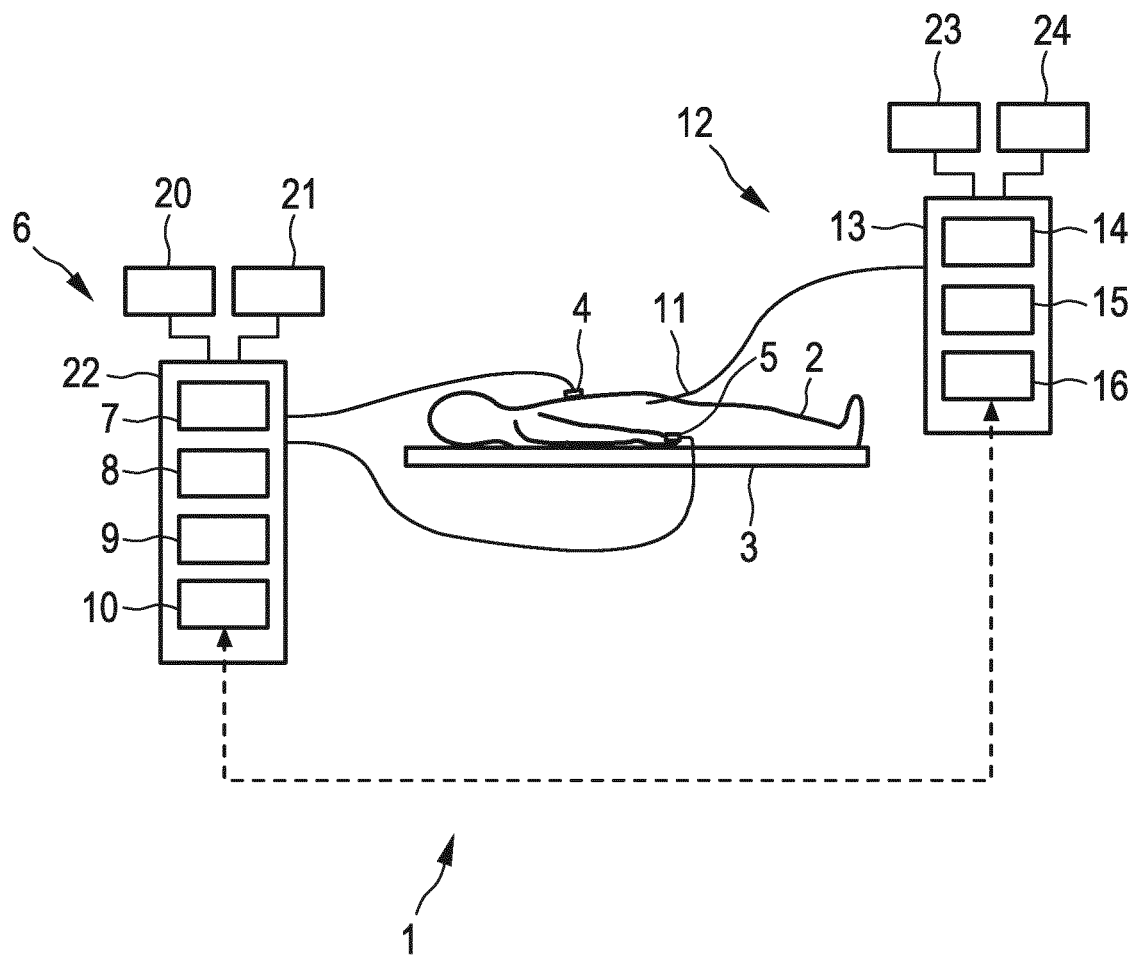
FIG. 1 shows schematically and exemplarily an embodiment of a system for monitoring a patient and for performing an electrical treatment procedure.

FIG. 1 shows schematically and exemplarily an embodiment of a system for monitoring a patient and for performing an electrical treatment procedure. The system 1 comprises a patient monitoring apparatus 6 and an electrical treatment apparatus 12. The patient monitoring apparatus 6 comprises a first measuring unit 7 for performing an electrical measurement of a physiological property of a patient 2 lying on a patient table 3, while an electrical treatment procedure is not performed. The patient monitoring apparatus 6 further comprises a second measuring unit 8 for performing a non-electrical measurement of the physiological property of the patient 2, while the electrical treatment procedure is performed. The first and second measuring units 7, 8 are connected to sensors 4, 5 for performing the electrical and non-electrical measurements. In this embodiment the first measuring unit 7 is adapted to measure an electrocardiogram and to determine the heart rate of the patient 2 as the physiological property based on the electrocardiogram. Moreover, in this embodiment the second measuring unit is adapted to optically measure a photoplethysmogram and to determine the heart rate based on the measured photoplethysmogram. The second measuring unit 8 preferentially uses an optical photoplethysmogram sensor like a finger $SpO_2$ photoplethysmogram sensor for measuring the photoplethysmogram and hence the heart rate.

The patient monitoring apparatus 6 further comprises a data communication unit 10 for receiving a treatment indication, which indicates that the electrical treatment procedure will be performed, from the electrical treatment apparatus 12. The data communication between the patient monitoring apparatus 6 and the electrical treatment apparatus 12 can be a wired or wireless data communication. The patient monitoring apparatus 6 further comprises a controller 9 for controlling the patient monitoring apparatus 6 such that the measurement of the physiological property is switched from the electrical measurement to the non-electrical measurement, after the treatment indication has been received. The controller 9 is further adapted to control the patient monitoring apparatus 6 such that the data communication unit 10 sends a non-electrical measurement indication, which indicates that the second measuring unit 8 measures the physiological property, to the electrical treatment apparatus 12, after the measurement of the physiological property has been switched from the electrical measurement to the non-electrical measurement. Moreover, the controller 9 is adapted to control the patient monitoring apparatus 6 such that the data communication unit 10 receives a completion indication, which indicates that the electrical treatment procedure has been completed, from the electrical treatment apparatus 12 and the measurement of the physiological property is switched from the non-electrical measurement to the electrical measurement, after the completion indication has been received.

The patient monitoring apparatus 6 further comprises an input device 20 like a keyboard, a computer mouse, a touchpad, et cetera and an output device 21 like a display, wherein the measured physiological property is shown on the output device 21. The patient monitoring apparatus 6 can comprise a casing 22 in which the first and second measuring units 7, 8, the data communication unit 10 and the controller 9 may be located. The input device 20 and the output device 21 might be external devices, which are not integrated into the casing 22, or the input device 20 and/or the output device 21 might be integrated into the casing 22.

The electrical treatment apparatus 12 comprises an electrical energy source 14 for providing electrical energy to a treatment device 11 for performing the electrical treatment procedure and a data communication unit 16 for sending a treatment indication, which indicates that the electrical treatment procedure will be performed, to the patient monitoring apparatus 6. In this embodiment the electrical energy source 14 is adapted to provide radiofrequency energy to an electrosurgical instrument 11 for performing an electrosurgical procedure as the electrical treatment procedure. The electrical treatment apparatus 12 further comprises a controller 15 for controlling the electrical treatment apparatus 12 such that the data communication unit 16 sends the treatment indication to the patient monitoring apparatus 6, before the electrical treatment procedure is performed. The controller 15 is further adapted to control the electrical treatment apparatus 12 such that the data communication unit 16 receives a non-electrical measurement indication, which indicates that the second measuring unit 8 of the patient monitoring apparatus 6 measures the physiological property, from the patient monitoring apparatus 6 and the electrical energy source 14 provides the electrical energy, after the non-electrical measurement indication has been received. Moreover, the controller 15 is adapted to control the electrical treatment apparatus 12 such that the data communication unit 16 sends a completion indication, which indicates that the electrical treatment procedure has been completed, to the patient monitoring apparatus 6, after the electrical treatment procedure has been completed.

The electrical treatment apparatus 12 comprises a casing 13 in which the electrical energy source 14, the controller 15 and the data communication unit 16 might be integrated. The electrical treatment apparatus 12 further comprises an input device 23 and an output device 24. The input device 23 can include, for instance, a foot switch, a keyboard, a computer mouse, a touchpad, et cetera. The output device 24 is preferentially a display for displaying, for instance, parameters characterizing the electrical treatment procedure like the applied current. The electrical treatment apparatus 12 is adapted such that the input device 23 provides a user interface for allowing a user like a physician to indicate that the electrical treatment procedure will be started, wherein the controller 15 can be adapted to control the electrical treatment apparatus 12 such that the data communication unit 16 sends the treatment indication, after the user has indicated that the electrical procedure will be started. The output device 24 can be an external device being not integrated in the casing 13 of the electrical treatment apparatus 12 or it can be integrated into the casing 13.

Figure 2:
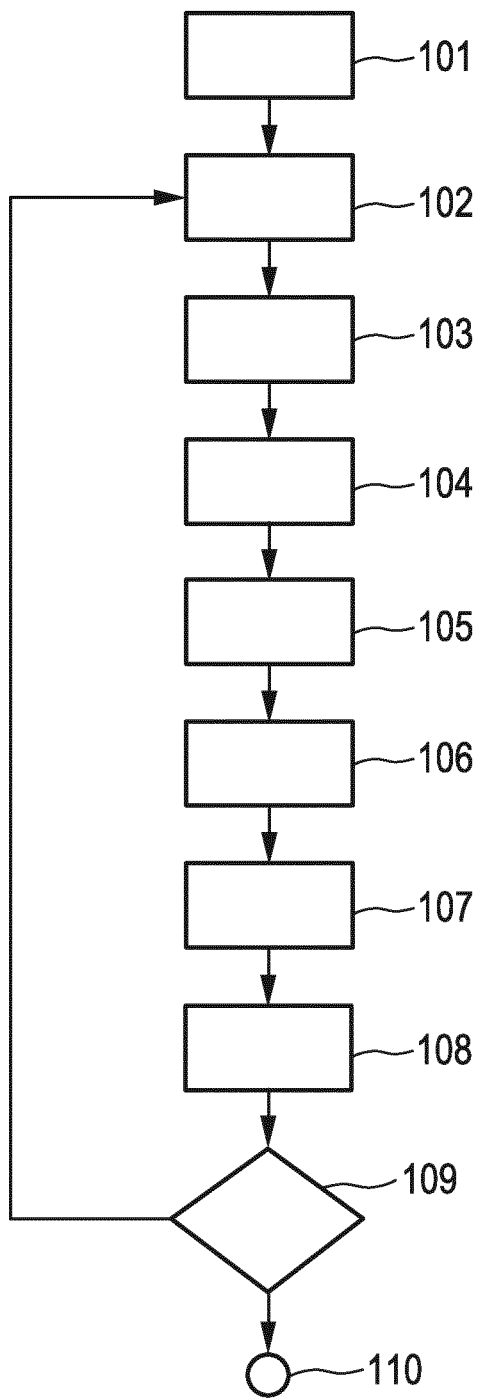
FIG. 2 shows a flowchart exemplarily illustrating an embodiment of a method for monitoring a patient and for performing an electrical treatment procedure.

In the following an embodiment of a method for monitoring a patient and for performing an electrical treatment procedure will exemplarily be described with reference to a flowchart shown in FIG. 2.

In step 101 the system 1 for monitoring a patient and for performing an electrical treatment procedure is initialized such that the first measuring unit 7 electrically measures the physiological property of the patient 2, i.e. by measuring an electrical physiological activity, and the electrical treatment apparatus 6 is ready for performing the electrical treatment procedure. In step 102 the treatment apparatus 12 receives via the user interface, i.e. via the input device 23, an indication from the user that the electrical treatment procedure should start. In particular, the user actuates a foot switch, because he wants the electrical energy source 14 to provide the electrical energy for performing the electrical treatment procedure. In step 103 the data communication unit 16 of the electrical treatment apparatus 12 sends a treatment indication, which indicates that the electrical treatment procedure will be performed, to the patient monitoring apparatus 6 and the data communication unit 10 of the patient monitoring apparatus 6 receives the treatment indication. In step 104 the measurement of the physiological property is switched from the electrical measurement to the non-electrical measurement, and in step 105 the data communication unit 10 of the patient monitoring apparatus 6 sends a non-electrical measurement indication, which indicates that the second measuring unit 8 non-electrically measures the physiological property, to the electrical treatment apparatus 12 and the data communication unit 16 of the electrical treatment apparatus 12 receives this non-electrical measurement indication.

In step 106 the electrical energy source 14 provides the electrical energy such that the electrical treatment procedure is performed and, after the provision of the electrical energy has been stopped, i.e. after the electrical treatment procedure has been completed, in step 107 the data communication unit 16 sends a completion indication, which indicates that the electrical treatment procedure has been completed, to the patient monitoring apparatus 6 and the data communication unit 10 of the patient monitoring apparatus 6 receives this completion indication. In step 108 the patient monitoring apparatus 6 switches from the non-electrical measurement to the electrical measurement. In step 109 it is checked whether the electrical treatment procedure should be performed again, i.e. if the electrical energy source 14 should provide electrical energy a further time or not. In particular, it is checked whether the user has indicated via the input device 23 or another input element that a further application of the electrical energy is not intended. If this is the case the method ends in step 110. Otherwise, the method can continue with step 102.

Step 101, the receiving of the treatment indication in step 103, step 104, the sending of the non-electrical indication in step 105 and the receiving of the completion indication in step 107 and step 108 can be regarded as being steps of a patient monitoring method for monitoring a patient by using the patient monitoring apparatus 6. The sending and receiving actions can be regarded as defining steps of a communication method for communicating between the patient monitoring apparatus 6 and the electrical treatment apparatus 12.

The above described system, apparatuses and methods allow for a reconfiguration of patient monitoring settings from, for instance, electrocardiogram to photoplethysmogram based heart rate detection during electrosurgical or electrocautery procedures automatically by means of networking the patient monitoring apparatus with the electrosurgical equipment, i.e. with the electrical treatment apparatus. When the user, who is preferentially a surgeon, activates an electrosurgical device, i.e. the treatment device 11, firstly a message can be sent to the patient monitoring apparatus informing the patient monitoring apparatus that radiofrequency energy is going to be generated soon. The patient monitoring apparatus can then automatically reconfigure its heart rate source from electrocardiogram to photoplethysmogram and send back an acknowledge message to the electrosurgical equipment that it is now safe for the patient to start producing radiofrequency energy. When the electrosurgical procedure is finished, the reverse communication can take place and the patient monitoring apparatus can reconfigure its heart rate signal source to electrocardiogram. For the data communication known standards for dynamic plug and play networking of medical devices like the OR.NET standard might be used.

During electrosurgical procedures the application of radiofrequency energy to the patient tissue frequently is disturbing electrocardiogram based heart rate monitoring, thereby leaving the patient's heart rate unmonitored during the electrosurgical procedure. This is critical for the patient's safety as both the user, i.e. in this case the surgeon, and a generally also present anesthesiologist are not able to see any reaction of the patient's heart rate to the surgical procedure. By providing the automatic reconfiguration of the heart rate monitoring as described above, the patient's safety can be vastly increased during the electrosurgical procedure. This reconfiguration process uses the networked medical devices sending messages preferentially based on user interface actions to each other, wherein the sending of messages can be a broadcast sending or a sending to dedicated recipients. The networked medical device, i.e. the patient monitoring apparatus, reconfigures automatically based on the received network messages. The user interface action can be provided via a foot switch or a trigger at an electrosurgical instrument, but also a button on a touch screen or on another input device might be used for allowing the user to provide the user interface action indicating that the electrical energy should be provided. Once, for instance, a surgeon triggers the electrosurgical equipment by pressing the foot switch or pulling a trigger, the electrosurgical equipment first sends a message on the device network, in order to inform the connected devices, especially the patient monitoring apparatus, that soon radiofrequency energy will be applied. The receiving device will take action on the received message, in particular the patient monitoring will reconfigure its heart rate detection automatically from electrocardiogram to photoplethysmogram detection. When this reconfiguration is finished, the patient monitoring apparatus will send back a message to the electrosurgical equipment which in turn will start with applying the radiofrequency energy to the patient. When the surgeon stops the radiofrequency energy application by, for instance, releasing the trigger of the surgical instrument or by not actuating the foot switch anymore, the electrosurgical equipment will again send a message to the networked patient monitoring apparatus, in order to inform this apparatus that the application of the radiofrequency energy has been stopped. The patient monitoring apparatus will receive this image and reconfigure its heart rate detection from photoplethysmogram based to electrocardiogram based detection.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The control of the system for monitoring a patient and for performing an electrical treatment procedure in accordance with the method for monitoring a patient and for performing an electrical treatment procedure and/or the control of the patient monitoring apparatus in accordance with the patient monitoring method and/or the control of the electrical treatment apparatus in accordance with the communication method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a patient monitoring apparatus comprising a first measuring unit for performing an electrical measurement of a physiological property like an electrocardiogram measurement providing a heart rate, while an electrical treatment procedure is not performed, and a second measuring unit for performing a non-electrical measurement of the physiological property like an optical photoplethysmogram measurement providing the heart rate. A data communication unit is adapted to receive a treatment indication, which indicates that the electrical treatment procedure will be performed, from an electrical treatment apparatus, and a controller is adapted to control the patient monitoring apparatus such that the measurement of the physiological property is switched from the electrical measurement to the non-electrical measurement, after the treatment indication has been received. This allows for an improved patient monitoring, because the likelihood of disturbance by, for instance, electrical noise can be significantly reduced.

The invention claimed is:

1. A patient monitoring apparatus for monitoring a patient, wherein the patient monitoring apparatus comprises:
    a first measuring unit adapted to perform an electrical measurement of a physiological property of a patient, only while an electrical treatment procedure is not performed,
    a second measuring unit adapted to perform a non-electrical measurement of the physiological property of the patient, only while the electrical treatment procedure is performed,
    a data communication unit adapted to receive a treatment indication, which indicates that the electrical treatment procedure will be performed, from an electrical treatment apparatus,
    a controller adapted to control the patient monitoring apparatus such that the measurement of the physiological property is switched from the electrical measurement to the non-electrical measurement, only after at least the treatment indication has been received.

2. The patient monitoring apparatus as defined in claim 1, wherein the controller is adapted to control the patient monitoring apparatus such that the data communication unit sends a non-electrical measurement indication, which indicates that the second measuring unit measures the physiological property, to the electrical treatment apparatus, after the measurement of the physiological property has been switched from the electrical measurement to the non-electrical measurement.

3. The patient monitoring apparatus as defined in claim 1, wherein the controller is adapted to control the patient monitoring apparatus such that the data communication unit receives a completion indication, which indicates that the electrical treatment procedure has been completed, from the electrical treatment apparatus and the measurement of the physiological property is switched from the non-electrical measurement to the electrical measurement, after the completion indication has been received.

4. The patient monitoring apparatus as defined in claim 1, wherein the second measuring unit is adapted to optically measure the physiological property.

5. The patient monitoring apparatus as defined in claim 1, wherein the first and second measuring units are adapted to measure the heart rate of the patient as the physiological property.

6. The patient monitoring apparatus as defined in claim 5, wherein the first measuring unit is adapted to measure an electrocardiogram for measuring the heart rate.

7. An electrical treatment apparatus for performing an electrical treatment procedure, wherein the electrical treatment apparatus comprises:
  an electrical energy source adapted to provide electrical energy to a treatment device adapted to perform the electrical treatment procedure,
  a data communication unit adapted to send a treatment indication, which indicates that the electrical treatment procedure will be performed, to a patient monitoring apparatus,
  a controller adapted to control the electrical treatment apparatus such that the data communication unit sends the treatment indication to the patient monitoring apparatus, before the electrical treatment procedure is performed;
  wherein the patient monitoring apparatus is adapted to switch between a first measuring unit adapted to perform an electrical measurement of a physiological property of the patient only while the electrical treatment procedure is not being performed and a second measuring unit adapted to perform a non-electrical measurement of the physiological property of the patient only while the electrical treatment procedure is being performed, based at least on the received treatment indication.

8. The electrical treatment apparatus as defined in claim 7, wherein controller is adapted to control the electrical treatment apparatus such that the data communication unit receives a non-electrical measurement indication, which indicates that the second measuring unit of the patient monitoring apparatus measures the physiological property, from the patient monitoring apparatus and the electrical energy source provides the electrical energy, after the non-electrical measurement indication has been received.

9. The electrical treatment apparatus as defined in claim 7, wherein controller is adapted to control the electrical treatment apparatus such that the data communication unit sends a completion indication, which indicates that the electrical treatment procedure has been completed, to the patient monitoring apparatus, after the electrical treatment procedure has been completed.

10. The electrical treatment apparatus as defined in claim 7, wherein the electrical treatment apparatus comprises a user interface for allowing a user to indicate that the electrical treatment procedure will be started, wherein the controller is adapted to control the electrical treatment apparatus such that the data communication unit sends the treatment indication, after the user has indicated that the electrical procedure will be started.

11. A system for monitoring a patient and for performing an electrical treatment procedure, wherein the system comprises:
  an electrical treatment apparatus adapted to perform the electrical treatment procedure, and a patient monitoring apparatus adapted to monitor a patient, wherein the patient monitoring apparatus comprises:
    a first measuring unit adapted to performing an electrical measurement of a physiological property of a patient, only while an electrical treatment procedure is not performed,
    a second measuring unit adapted to perform a non-electrical measurement of the physiological property of the patient, only while the electrical treatment procedure is performed,
    a data communication unit adapted to receive a treatment indication, which indicates that the electrical treatment procedure will be performed, from an electrical treatment apparatus,
  a controller adapted to control the patient monitoring apparatus such that the measurement of the physiological property is switched from the electrical measurement to the non-electrical measurement, only after at least the treatment indication has been received.

* * * * *